United States Patent [19]

Mufti et al.

[11] 4,380,476

[45] Apr. 19, 1983

[54] PROCESS FOR THE PREPARATION OF 4,1',6'-TRICHLORO-4,1',6'-TRIDEOXYGALACTOSUCROSE (TGS)

[75] Inventors: Khizar S. Mufti, Reading; Riaz A. Khan, Sonning, both of England

[73] Assignee: Talres Development (N.A.) N.V., Netherlands Antilles

[21] Appl. No.: 275,593

[22] Filed: Jun. 19, 1981

[30] Foreign Application Priority Data

Jul. 8, 1980 [GB] United Kingdom ................ 8022320

[51] Int. Cl.³ .......................... C07H 5/02; C07H 1/06
[52] U.S. Cl. ..................................... 127/46.3; 127/30;
127/42; 536/122; 536/119
[58] Field of Search ....................... 536/122, 115, 119;
127/30, 29, 42, 46.2, 46.3

[56] References Cited

U.S. PATENT DOCUMENTS

| | | | |
|---|---|---|---|
| 4,117,224 | 9/1978 | Khan et al. | 536/119 |
| 4,262,115 | 4/1981 | Khan et al. | 536/122 |

FOREIGN PATENT DOCUMENTS

| | | | |
|---|---|---|---|
| 4202828 | 12/1964 | Japan | 536/115 |
| 55-22700 | 2/1980 | Japan | 536/119 |
| 1543167 | 3/1979 | United Kingdom | |
| 2065648 | 7/1981 | United Kingdom | 536/122 |

OTHER PUBLICATIONS

Fairclough et al.; Carbohydrate Research, 40 (1975) 285–298.
Kononenko et al.; Journal of Applied Chemistry, 11 (1961) 7–10.

*Primary Examiner*—Kenneth M. Schor
*Attorney, Agent, or Firm*—Ostrolenk, Faber, Gerb & Soffen

[57] ABSTRACT

A process for the preparation of 4,1',6'-trichloro-4,1',6'-trideoxygalactosucrose (TGS) comprising the steps of:
(a) reacting sucrose with an acylating reagent under conditions to provide a mixture of acylated sucrose derivatives containing a major proportion of 6-monoacylated material;
(b) optionally separating 6-monoacylated sucrose derivative from other acylated derivatives before step (c);
(c) reacting the monoacylated sucrose derivative with a chlorinating reagent capable of chlorinating at positions 1', 4 and 6' of a sucrose 6- acylate; and
(d) deacylating and separating (in either order) the 4,1',6'-trichloro-4,1',6'-trideoxygalactosucrose material formed.

14 Claims, No Drawings

PROCESS FOR THE PREPARATION OF 4,1′,6′-TRICHLORO-4,1′,6′-TRIDEOXYGALACTOSUCROSE (TGS)

This invention relates to a process for the preparation of the potent sweetener 4,1′,6′-trichloro-4,1′,6′-trideoxygalactosucrose.

The above-mentioned trichlorogalactosucrose is a potent sweetener, having a sweetness several hundreds of times that of sucrose. Its use as a sweetener and sweetening compositions containing it are disclosed in British Patent Specification No. 1,543,167. Preparation of 4,1′,6′-trichloro-4,1′,6′-trideoxygalactosucrose (hereinafter referred to as TGS) involves the substitution of chlorine atoms in the sucrose molecule in one of the five secondary hydroxyl positions and in two of the three primary hydroxy positions. This particular selection of positions means that any synthetic route must involve the preparation of an intermediate sucrose derivative having the required positions available for chlorination, while other positions are blocked. In particular, the reactive 6-position must not be chlorinated, while the 4-position must be rendered available for chlorination.

One route proposed in the literature (Fairclough et al, Carbohydrate Research 40 (1975) 285–298) involves the formation of the 6,1′,6′-trityl derivative of sucrose, peracetylation of the molecule and then de-tritylation with migration of the 4- acetyl radical to the 6- position, to give 2,3,6,3′,4′-penta-O-acetylsucrose which has the correct hydroxy groups unprotected. Subsequent reaction with a chlorinating agent provides the 4,1′,6′-trichlorogalactosucrose penta-acetate which in turn yields TGS on elimination of the acetyl groups. The chlorination proceeds with inversion of configuration. The 1′ and 6′- positions freely rotate, but the 4- position cannot and the glucose ring is thus inverted at the 4- position into a galactose ring so that the product is a galactosucrose.

The reaction sequence involving the simultaneous de-tritylation and acetyl shift contains, in all, a relatively high number of stages, and the initial tritylation reaction is undesirable from an economic point of view. There is thus a need for a process which will give the desired sweetener in a reasonable yield from sucrose in a small number of stages.

One of the main problems in designing a process for the preparation of TGS is trying to design a protected intermediate which has the required 4, 1′ and 6′ positions available for chlorination, while other positions are either inactive or are protected. In particular, the reactive 6-position must always be protected unless the 4- position is already chlorinated.

Attempts to protect only the 6- position meet the problem that the 6′- position is usually similarly reactive and it is difficult to produce the required derivative in a selective manner.

The present invention is based on a radical approach to the overall problem, and is based on the finding that careful monoacylation of sucrose will give a mixture of sucrose monoacylates (together, inevitably, with some higher acylates, but containing a substantial proportion of the 6-monoacylate) and that, if the mixed acylated derivative is chlorinated, it is possible to separate the required TGS from the other products produced, without undue difficulty.

According to the present invention, there is provided a process for the preparation of 4,1′,6′-trichloro-4,1′,6′-trideoxygalactosucrose (TGS) comprising the steps of:
  (a) reacting sucrose with an acylating reagent under conditions to provide a mixture of acylated sucrose derivatives containing a major proportion of 6-monoacylated material;
  (b) optionally separating 6-monoacylated sucrose derivative from other acylated derivatives before step (c);
  (c) reacting the monoacylated sucrose derivative with a chlorinating reagent capable of chlorinating at positions 1′, 4 and 6′ of a sucrose 6- acylate; and
  (d) deacylating and separating (in either order) the 4,1′,6′-trichloro-4,1′,6′-trideoxygalactosucrose material formed.

The acylating agent used may be any acylating reagent which will produce an ester of sucrose which will be stable to the chlorinating reagent to be used in step (c) and which can be subsequently hydrolysed without difficulty. In general, a reagent serving to form an aliphatic, araliphatic or aryl carboxylate is suitable. Particularly suitable carboxylates include lower alkyl carboxylates such as acetates and propionates; and aryl carboxylates such as benzoates.

The acylating reagent may be any active derivative of the relevant acid, and in the case of carboxylic acylation is preferably an acyl anhydride or acyl halide. Other reagents include enyl acylates or other suitably active esters.

The reaction conditions for the acylation will, of course, depend on the nature of the acylating reagent. Reaction of sucrose with a carboxylic anhydride, such as acetic anhydride, is conveniently effected in the presence of a base, particularly a basic tertiary amine solvent, such as pyridine. Reaction with an acyl halide may be effected under similar conditions to the reaction with an anhydride, or alternatively may utilise aqueous alkaline conditions (e.g. the well-known Schotten-Baumann conditions).

Reaction with an enyl ester is conveniently effected in the absence of water and in the presence of no more than a trace of a base catalyst, in a polar aprotic solvent. These conditions, which are described and claimed in British Patent Application No. 2 052 492A, have been found to produce a good yield of monoesterified sucrose as compared with aqueous and strongly basic conditions which tend to give uncontrolled higher esterification. Acid conditions are unsuitable as the sucrose tends to be hydrolysed into monosaccharide fragments.

Where the acyl substituent is a longer chain aliphatic carboxylic acyl, e.g. a fatty acid carboxylate, the acylation reaction is conveniently effected using the fatty acid halide under basic conditions, or by means of a transesterification, particularly using a lower alkyl ester of the fatty acid, e.g. the methyl ester. The fatty acid itself may comprise a single fatty acid having, e.g., 8 or more carbon atoms in the aliphatic chain, particularly 10 to 18 carbon atoms. Alternatively, the fatty acid may comprise a mixture of fatty acids derived from a naturally occurring triglyceride, e.g. tallow fatty acids, coconut fatty acids or palm fatty acids. The transesterification reaction may be effected by any of the methods well known in the sucrose ester art, particularly base-catalysed reactions in a solvent such as dimethylformamide, or a solvent-free reaction at atmospheric pressure, such as that of British Pat. No. 1,339,053. Other acylation reagents include trichloroacetyl chloride, benzoyl cyanide, propionic anhydride and butyric anhydride.

The success of the overall process of this invention relies on the mono-acylation producing a major proportion of 6- acylate. Thus, in any of the above-mentioned methods of acylation, the acylation should be effected in such a way that not only is mono-acylation the predominant reaction, but also that as much as possible of the mono-acylation is at the 6-position rather than elsewhere. Mono-acylation can be maximised by controlling the reaction, e.g. by maintaining the sucrose in excess throughout the addition of the acylating agent, or by using a very low reaction temperature.

It is a particularly preferred feature of the invention that the acylation is effected using acetic anhydride in a tertiary amine base such as pyridine. We have found that this system is particularly specific for 6-acetylation, whereas other systems (e.g. benzoyl chloride under aqueous conditions) are less specific and give a mixture of monoesters. In particular, the 6-acetate can be prepared in predominance by reacting sucrose with acetic anhydride at a temperature below about $-20°$ C., e.g., of from $-20°$ to $-75°$ C., preferably $-25°$ to $-45°$ C., in a tertiary amine base such as pyridine. If very low temperatures are required, it is necessary to dilute the system with an inert solvent to dissolve the pyridine and prevent it freezing solid. A ketone such as methyl ethyl ketone (MEK) or acetone is convenient. In a most preferred embodiment of the process, sucrose is dissolved in the minimum of pyridine (approximately 1:12.5 by weight) to form a hot solution which is cooled to about $-35°$ C. Acetic anhydride (a slight molar excess) is then gradually added and the mixture is agitated for several hours, typically about 6 hours. Such a method gives a reaction mixture containing about 40% of the 6-acetate (about 40% yield).

The chlorination reaction may be effected on the mixed acylated product obtained in the first step, without any isolation or separation of products at that stage, but alternatively, the 6-acyl derivative can be isolated before chlorination, e.g. by chromatography. The chlorinating reagent may be any suitable reagent capable of chlorinating a sucrose 6-acylate in the 1'-, 4- and 6'-positions. A preferred chlorinating reagent, for its ease of use and its selectivity, is a reagent of the Vilsmaier type, i.e. an N,N-dialkyl-(chloromethaniminium) chloride of the general formula:

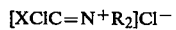

where R represents an alkyl group, typically a methyl or ethyl group, and X represents a hydrogen atom or a methyl group.

Reagents of this type are prepared by reaction of an inorganic acid chloride with an N,N-dialkylformamide or N,N-dialkylacetamide. The inorganic acid chloride may typically be phosphorous pentachloride, phosgene, or thionyl chloride.

It is particularly surprising that this reagent will safely chlorinate in the 4',1'- and 6'-positions of a sucrose molecule as this class of acidic reagent is in general well known for its specificity as a chlorinator of more active primary hydroxy compounds. Thus, e.g. when N,N-dimethyl-(chloromethaniminium) chloride was reacted with uridine, 5-chloro-uridine was obtained with no apparent chlorination in the two possible secondary positions (Dods & Roth, Tetrahedrom Letters, 165–168, 1969). Furthermore, reaction of a saccharide in which the primary hydroxy group and three of the four available secondary hydroxy groups had been protected by acetalation to leave one free secondary hydroxy group yielded, in fact, the chlorinated product in which the primary hydroxy group had been replaced by chlorine, the protecting acetal having shifted to the secondary position. Thus, 1,2:5,6-O-di-isopropylidene-α-D-glucofuranose gave 6-chloro-6-deoxy-1,2:3,5-O-di-isopropylidene-α-D-glucofuranose in a yield exceeding 70% (Hanessian and Plessas, J. Org. Chem. 34, 2163–2170, 1969).

We have found that the reagents in question can be reacted with 6-O-acetyl sucrose to give the corresponding 4,1',6'-trichloro derivative (i.e. TGS monacetate) in good yield, e.g. about 65%.

The reagents may be prepared by reacting an inorganic acid chloride with an N,N-dialkylamide of the formula $R_2NCOX$, where R and X are as defined above. The reagents may be formed in situ, but are preferably prepared in advance and isolated before being used. The inorganic acid chloride may be, for example, thionyl chloride, phosphorus oxychloride, or sulphuryl chloride, but the acid chloride of choice is phosphorus pentachloride (giving the reagent $(Me_2N=CHCl)^+ Cl^-$). The amide is preferably a formamide (X=H) such as dimethyl formamide (dmf). The reagent is preferably prepared by adding n kg of $PCl_5$ to vigorously stirred cold dmf (about 1.5 n liters) keeping the temperature below 50° C. The mixture is then agitated for about one hour with cooling at about 0° C. and the resulting crystalline material is filtered off, washed and dried under vacuum. The reaction with the sucrose 6-acetate is then preferably effected in a solvent such as dmf itself (for homogeneity of the system) or an inert solvent such as a chlorohydrocarbon, e.g. trichloroethane, or an aralipathic hydrocarbon, e.g. toluene or xylene.

The concentration of the sucrose monoester in the chlorinating medium is suitably from 5 to 45%, preferably about 12–15% by weight. The amount of Vilsmeier reagent used is preferably about 21 to 45 moles per mole of monoester, i.e. about 7 to 15 molar equivalents. An amount of about 33 moles per mole of monoester is optimal. It is important that water is prevented from contacting the reagent, and for this reason the monoester solution and the reagent solution should preferably be dried, and the reaction vessel should be fitted with a drying tube.

The chlorination reaction is exothermic and it is thus desirable to add a cooled solution of the monoester slowly to the reagent solution, with cooling, so that the actual reaction temperature is held between 100° and 140° C. The preferred range is from 115°–125° C. as lower temperatures lead to slow reactions, while higher temperatures lead to decomposition of the sucrose.

The Vilsmeier chlorination is preferably worked up by neutralisation and hydrolysis with an alcohol/base mixture, e.g. methanolic ammonium hydroxide (2:1 by weight).

Another chlorinating reagent which may be used is sulphuryl chloride, which reacts initially to form chlorosulphate esters of available hydroxy groups. These chlorosulphate esters are then subsequently or simultaneously decomposed with inversion of configuration, to provide the corresponding chlorodeoxy derivative. Conveniently, the chlorosulphated intermediates may be isolated, e.g. by pouring the reaction mixture into ice-cold sulphuric acid solution and extracting the acid with a solvent such as chloroform. The product obtained may be dechlorosulphated in the usual way, e.g. by treatment with a catalytic amount of an iodide such as sodium iodide, preferably in the cold. Sulphuryl chloride is, however, less selective than the Vilsmeier reagents, which are accordingly preferred.

As stated above in the general definition of the process of the invention, the separation of the required 6-acylate from other acylates can be effected before or after chlorination. Most preferably, the initial mixture of acylates obtained from step (a) is separated in step (b) to give a fraction which consists of, or is rich in, the required 6-acylate. This separation can be effected by chromatography, for example on silica gel. However, it is a preferred feature of the present invention, that the separation in step (b) is effected by ion exchange resin chromatography. Any suitable ion exchange resin may be used, and the art of separation of saccharides on such resins is well documented. A polystyrene sulphonic acid cation exchange resin is particularly suitable, for example one cross-linked with 4% of divinyl benzene, e.g. Dowex 50×4 produced by the Dow Chemical Company. The resin is used in the base form, conveniently prepared by slurrying the resin with ammonia. The resin is conveniently used in a column and is eluted with a suitably polar solvent typically a mixture of a polar organic solvent and water, e.g. aqueous acetone. In such a system, the reaction products and starting materials in the acylation reaction can be easily and efficiently separated. The first substances to be eluted are the less polar di- and higher esters and also any pyridine or other base from the acylation. These are followed by the monoacylates in a main peak, followed in turn by unreacted sucrose.

Deacylation may be effected by any method known per se and the method chosen will depend to a certain extent on the nature of the acyl group. Carboxylates are conveniently removed by treatment with a base such as sodium methoxide in an alcoholic medium such as methanol.

However, it is a preferred feature of the process of the present invention, that the chlorinated material is isolated after first being peracylated. Thus, for example, the trichloro-monoacetate intermediate is preferably fully acetylated in situ by reaction with acetic anhydride in pyridine to give the trichloro pentaacetate (TGSPA). This material can then be extracted from an aqueous work-up system, using a solvent such as ethyl acetate or toluene, crystallised, and de-esterified.

The process is preferably effected with step (b), with the use of a Vilsmeier chlorinating reagent, and with peracetylation of the chlorinated material. Under those conditions, the chlorinated saccharide material is predominantly TGSPA and can be easily separated by extraction and crystallisation.

Alternatively, the success of the overall process according to the present invention will depend in part on the fact that TGS itself can be isolated without undue difficulty from the deacetylated mixture of chlorinated sucrose derivatives obtained. We have found that chromatography, e.g. on silica gel, will isolate TGS relatively simply. For example, elution of the deacylated mixture with a series of eluants of increasing polarity removes first the less polar by-products and then TGS, while more polar compounds remain bound. Mixtures of chloroform and acetone are particularly suitable: a 2:1 mixture followed by a 1:1 mixture is effective in isolating TGS in the 1:1 eluate. We prefer to chromatograph after deacylation, but chromatographic separation of TGS 6-acylate is also possible. Alternatively, the deacylated material can be partitioned between solvents such as ethyl acetate and water, or chloroform and water to achieve a preliminary separation of trichlorinated sucrose from by-products. Partition between chloroform and water causes the higher chlorinated material and chlorinated pyridine (a by-product of the sulphuryl chloride/pyridine reaction) to enter the chloroform layer, while TGS and 1',4-dichloro-1',4-dideoxysucrose (DGS) enter the water, DGS may thus be recovered as a useful by-product from a TGS synthesis as described above.

The following examples illustrate the invention:

EXAMPLE 1

(a) PARTIAL ACETYLATION OF SUCROSE

Sucrose (2.0 g) was dissolved in pyridine (30 ml) by boiling for 15 minutes. The solution was cooled to room temperature and acetic anhydride (0.606 mls; 1.1 M.E. (molar equivalent)) added thereto. The reaction mixture was kept at room temperature for 1 hours. T.l.c. ($CHCl_3$:MeOH; 2:1) showed three faster moving products, the fastest being very minor, but the remaining two in almost equal quantities. There was also approximately 25% unreacted sucrose. All the acetic anhydride was consumed in this time and assays showed that the yield of 6-acetate at this stage was about 50%.

(b) CHLORINATION OF THE PARTICALLY ACETYLATED SUCROSE

To the above reaction mixture, chloroform (30 ml) was added and the contents cooled to −75° C. in a dry ice/acetone bath. The chloroform was added primarily to prevent freezing of pyridine but also to slow down the reaction and thus allow better control over the reaction. Sulphuryl chloride (30 M.E., i.e. 14.2 ml) was then added to the cooled reaction mixture dropwise over a period of 1.5 hours. The reaction mixture was then allowed to warm to room temperature and left at that temperature for 4 hours, after which time it was heated at 45° C. for 12 hours and then cooled to room temperature.

The mixture was poured into pre-cooled (about 4° C.) 10% sulphuric acid solution (100 ml) slowly with stirring. The sulphuric acid mixture was extracted twice with chloroform and the chloroform extracts washed twice with water, with saturated sodium hydrogen carbonate solution pH 7 and then twice with water, and dried over anhydrous sodium sulphate. The sodium sulphate was filtered off, the filtrate concentrated to a syrup, and the syrup was dissolved in methanol (50 ml). The methanol solution was then dechlorosulphated with a catalytic amount of NaI crystals, keeping the solution in an ice bath. Sulphates precipated. The solution was then neutralised with sodium carbonate to pH 7 and then the sulphates and carbonates were filtered off.

The filtrate was then deacetylated with sodium methoxide (1 N to pH 10 for 4 hours). T.l.c. in ethyl acetate:acetone:water; (6:6:1) showed TGS and several faster and slower moving products.

The mixture was concentrated and eluted from a column of silica gel (Merck Kieselgel 60 70–230 mesh ASTM, approx 75 g) using (chloroform:acetone; 2:1) initially and then (chloroform:acetone; 1:1) as eluant giving TGS in approximately 15% yield overall from the starting sucrose.

When the deacetylated syrup was partitioned between ether and water, most of the products faster moving than TGS went into the ether. The water extract was evaporated and subjected to t.l.c. (silica gel) to show the presence of from 18 to 22% of the water-soluble material as TGS.

In a similar reaction, the deacetylated syrup was partitioned between chloroform and water and the water layer was evaporated and examined by g.l.c. after conventional silylation. The extract was found to contain about 27% TGS and about 10% DGS.

EXAMPLE 2

A purified mixture of sucrose mono- and di-esters (5 g) obtained from transesterification of sucrose with tallow at atmospheric pressure at 130° C. in the absence of a solvent (according to U.K. Pat. No. 1,399,053 of Tate & Lyle Limited) was treated with sulphuryl chloride in the same molar proportion as in Example 1 and the mixture was worked up in a similar manner. T.l.c. (ethyl acetate:acetone:water; 6:8:1) showed the presence of TGS.

EXAMPLE 3

Sucrose (3.42 g, 10 mmole) and sodium carbonate (3.7 g, 35 mmole) were dissolved in water (60 ml). A solution of benzoyl chloride (2.9 ml, 25 mmole) in dichloromethane (20 ml) was added and the mixture stirred at room temperature for 2 hours. The aqueous layer was separated, neutralised with dilute HCl and evaporated to dryness to give a mixture of unreacted sucrose and two monobenzoylated compounds which were present in a ratio of 8:1. The mixture of monobenzoylated compounds was separated from the sucrose by elution through a silica gel column (Merck Kieselgel as before) using ethyl acetate/acetone/water 10:10:1.

The mixture of monobenzoylated compounds was then chlorinated using 30 molar equivalents of sulphuryl chloride, as described in Example 1. After de-esterification of the mixture, TGS was isolated by chromatography on silica gel (as before).

EXAMPLE 4

1. ACETYLATION

Sucrose (250 g) and pyridine (3.125 l) were added to a 5 liter flanged neck round bottom flask fitted with overhead stirrer, condenser and heating mantle. The mixture was stirred and heated over 20 min. to the boiling point when dissolution occurred. The flask was allowed to cool to room temperature over several hours without stirring, left overnight at room temperature and then cooled to −35° C. in an acetone bath. Both the cooling acetone and the flask contents were stirred with overhead stirrers. At −35° C., acetic anhydride (85 ml, 1.1 ME) was added and the temperature was maintained at −30° to −35° for 6 h. Water (20 ml) was added and the reaction mixture was allowed to come to room temperature overnight.

The reaction mixture was transferred to a 10 liter Buchi flask and concentrated at 50° at the water pump (10–40 mmHg) for 1 h (distillate approx. 3 liters) and under high vacuum (5–10 mmHg) for 1 h to give the product as a sticky solid (wt. approx. 380 g). Acetone-water (7:3, 400 ml) was added to the flask which was warmed to 50° C. and rotated until complete dissolution occured. The resulting solution was divided into two equal portions of approx. 360 ml, the Buchi flask being washed out with a further volume of approx. 50 ml of acetone-water. A sample (about 1 ml) of this material was concentrated to a syrup and submitted for analysis of sucrose 6-acetate content. (Analysis: about 40% sucrose 6-acetate). The remaining material was stored in a stoppered flask at 4° until required.

2. RESIN COLUMN SEPARATION

The resin used was Dowex 50×4, 50–100 mesh (dry), a polystyrene sulphonic acid cation exchange resin cross linked with 4% divinyl benzene obtainable from Sigma in the hydrogen form. The resin in the hydrogen form (3.8 kg) was slurried in water to a volume of 6 liters. Ammonia solution (S.G. 0.880, 900 ml) was added and stirred gently by hand. An excess of ammonia should then have been present. The resin was washed by decantation with demineralised water (4 liter lots) until ammonia free. The water was decanted off and the resin stirred with acetone (4 liters). The acetone was then decanted off and the resin stirred with 2×4 liters of 70% acetone (70 parts acetone+30 parts demineralised water). A glass QVF column 7.7 cm diameter×100 cm was fitted with top and bottom flange-to-cone (B34) adaptors. The bottom cone was fitted with a B34 socket and tap, the socket being packed with glass wool to support the resin. The top cone was fitted with a solvent delivery system. The resin slurry was poured in and allowed to settle. The resin bed height was 94 cm giving a resin volume of 4.4 liters. The column was washed with 70% acetone/water (20 liters) at 50 ml/min.

One half of the acetone/water solution from the acetylation was filtered under vacuum through glass fibre filter paper (Whatman GF/A) into a 500 ml Buchner flask to remove any resin contaminants. The solution was then run onto the resin surface using a separating funnel with an extended stem at such a rate that the resin bed was not disturbed and a well defined layer of sample solution was formed between the solvent and the resin. The column flow was reduced to 25 ml/min. at this stage. On completion of the sample addition, the flow rate was increased to 50 ml/min.

500 ml fractions were collected, the first fraction being started immediately when the sample solution reached the top of the resin. Fractions 1 to 4 were discarded and the rest were collected and examined by tlc. (CH$_2$Cl$_2$/MeOH 2:1). 36 fractions were collected with a total eluent volume of 18 liters. Those fractions containing the majority of the sucrose mono-acetate (generally 12–20) were concentrated together in a 10 liter Buchi flask at the water pump at 50° C. Fractions 11–18 gave 1.95 liters at 120–180 mmHg. The receiver emptied, and the water pump pressure went down to 10–20 mmHg and a further 1.03 liters of distillate was collected.

After the last fraction has been collected, the column is ready for immediate re-use with no regeneration required.

These operations were repeated with the second half of the acetone/water solution from the acetylation. Acetone (2×800 ml) was then added to the combined syrupy product and distilled off to remove the last traces of water. The resulting white foam was dried on the Buchi at 50° C. using a rotary vacuum pump (3–5 mmHg) for 30 min. The product was weighed (about 116 g), then dissolved in dmf (150 ml) and transferred to a 500 ml flask, the Buchi flask being washed out with further dmf (2×50 ml).

A small sample of this dmf solution was concentrated to dryness and analysed for sucrose 6-acetate by glc (about 85%).

3 A molecular sieve (30 g) was added to the dmf solution to remove last traces of water. After stirring for 1 h, the dmf solution was decanted off and the sieve washed with further dmf (2×50 ml).

3. CHLORINATION

Dmf (3 liters) was cooled to 0° in a 5 liter beaker and $PCl_5$ (2 kg) was added with vigorous stirring while the temperature was maintained below 50° C. The beaker was stirred at 0° for 1 h and the resulting crystals were filtered off in two parts, each part being washed with dmf (2×200 ml), then diethyl ether (500 ml). The crystals were dried under vacuum overnight and weighed (about 1400 g).

Dmf (600 ml) was added to the Vilsmeier reagent from 3(a) (about 500 g) in a 3 liter flange neck flask fitted with stirrer, thermometer, drying tube and cooling bath. The solution was cooled to 0° C. and the sucrose mono-acetate solution from step 2 (containing about 100 g) was added slowly, keeping the temperature below 20° C. The reaction was stirred at 0° C. for 15 min., then the flask was transferred to an oil bath at about 60° C. and nitrogen gas was bubbled through to assist with removal of HCl gas. The reaction was then heated and stirred over 1.5 h to 120° C. internal temperature (bath temperature about 126° C.), and this temperature maintained for a further 2.5 h.

During this heating period, the reaction was monitored by tlc ($CH_2Cl_2$/MeOH 4:1), the samples being pre-treated with ammonium hydroxide in methanol.

The reaction was then cooled to 20° C. and methanol/ammonium hydroxide (2:1, 600 ml) was added, the temperature being maintained below 50° C. The solvents were then evaporated on the Buchi at the water pump at 70° C. for 1 h, then under high vacuum (about 1 mmHg) at 70° C. for 1 h (total volume of distillate about 600 ml) to give a syrupy residue.

The syrupy residue was stirred with pyridine (1 liter) and acetic anhydride (1 liter) was added while the temperature was maintained below 60° C. When dissolution was complete, the reaction was stirred at 50° C. for 2 h. The reaction was cooled to 20° C. and methanol (200 ml) was added, maintaining the temperature below 60° C. The solution was then evaporated at 70° C. at the water pump for 1 h followed by about 4 h at high vacuum (5-7 mmHg) until about 1300 ml of distillate was collected.

The residue was extracted with hot (about 60° C.) toluene (4×1 liter). The toluene extracts were concentrated to a syrup (about 160 g) which was dissolved in ethyl acetate (500 ml). This ethyl acetate solution was washed with water (2×500 ml), and the water washings were themselves washed with ethyl acetate (2×250 ml). The combined ethyl acetate extracts were dried over anhydrous sodium sulphate and filtered through charcoal (about 60 g) which was washed with further ethyl acetate (500 ml). The ethyl acetate solutions were then concentrated to syrup (about 130 g, 60-70% TGSPA).

This syrup was dissolved in hot ethanol (250 ml) which was cooled to room temperature and seeded, then left overnight at room temperature. The resulting crystals were filtered off and dried (about 50 g, 90% pure). Recrystallisation from ethanol was carried out until the crystals were above 98% pure. (2 or 3 crystallisations required, final weight about 40 g).

4. DE-ACETYLATION

The TGSPA crystals (about 40 g) were dissolved in methanol (about 400 ml) so as to produce a 10% solution. 1 M sodium methoxide was added to pH 9 and the solution stirred at 20° for 4 h. Tlc ($CH_2Cl_2$/MeOH 4:1) revealed a single major spot corresponding to TGS. Amberlyst 15 ($H^+$) ion exchange resin was added to pH 7 and the solution was filtered and concentrated to dryness (wt. about 25 g). Distilled water (about 250 ml) was added so as to make a 10% solution which was filtered through a charcoal pad to give a clear colourless solution. The water was distilled off at the Buchi to give a dry syrup, and further water (about 9 ml) was added so as to give a 65% w/w solution. This was stirred and seeded. The resulting crystals were filtered off, washed quickly with a small volume of cold water and dried under vacuum below 40° C. Weight of crystals obtained about 10-20 g. (These figures represent a number of runs and thus yields are given as "about 40 g" or "about 10-20 g". The overall yield from sucrose was about 7%).

EXAMPLE 5

Sucrose (50 g) in pyridine (625 ml) diluted with methyl ethyl ketone (MEK) (400 ml) was cooled to −50° C. and treated with a solution of acetic anhydride (150 ml) in MEK (350 ml). The mixture was stirred at −50° C. for 17 hours and was then quenched with water and the solvent evaporated to give a residue (68 g) containing about 50% sucrose monoacetate. This material was then reacted with the Vilsmeier reagent of Example 4 under similar conditions to those used in Example 4. The product was deacylated in situ using methanolic sodium methoxide. An aqueous solution was then extracted with dichloromethane (to remove tetrachloro derivatives) and then with ethyl acetate. The crude TGS obtained was then peracetylated, crystallised as in Example 4, and deacetylated. Crystalline TGS of about 99% purity was obtained in about 5% yield overall.

We claim:

1. A process for the preparation of 4,1',6'-trichloro-4,1',6'-trideoxygalactosucrose (TGS) comprising the steps of:
   (a) reacting sucrose with an acylating reagent under conditions to provide a mixture of acylated sucrose derivatives containing a major proportion of 6-monoacylated material;
   (b) reacting the monoacylated sucrose derivative with a chlorinating reagent capable of chlorinating at positions 1',4 and 6' of a sucrose 6-acylate; and
   (c) deacylating and separating the 4,1',6'-trichloro-4,1',6'-trideoxygalactosucrose material formed.

2. The process of claim 1, wherein the acylating reagent in step (a) is selected from the group consisting of carboxylic acyl anhydrides, carboxylic acyl halides, and enyl acylates and lower alkyl fatty acid esters in the presence of a transesterification catalyst.

3. The process of claim 1, wherein the acylating reagent is acetic anhydride in a tertiary amine base.

4. The process of claim 3, wherein the step (a) is effected using acetic anhydride in pyridine at a temperature of −20° to −75° C.

5. The process of claim 1, wherein the chlorinating reagent in step (b) is selected from the group consisting of a Vilsmeier reagent and sulphuryl chloride.

6. The process of claim 5, wherein the chlorinating reagent is a Vilsmeier reagent of the formula:

[XClC=NR$_2$]$^+$Cl$^-$ (where R represents an alkyl group, and X represents a hydrogen atom or a methyl group).

7. The process of claim 6, wherein the chlorinating reagent is prepared by reacting phosphorus pentachloride with N,N-dimethylformamide.

8. The process of claim 1 in which the 6-monoacylated sucrose derivative is separated from other acylated derivatives before step (b).

9. The process of claim 8, wherein the separation of acylated material before step (b) is effected using ion-exchange resin chromatography.

10. The process of claim 9, wherein the resin used is a polystyrene sulphuric acid cation exchanged resin used in the base form.

11. The process of claim 1, wherein the chlorinated material from step (b) is peracylated before separation and purification.

12. The process of claim 11, wherein the chlorinated material obtained after hydrolysis of the chlorinating agent is peracetylated in situ using acetic anhydride in pyridine.

13. The process of claim 1 wherein the separation in step (c) is effected before the deacylation.

14. A process for the preparation of 4,1',6'-trichloro-4,1',6'-trideoxygalactosucrose (TGS) comprising the steps of:
 (a) reacting sucrose with acetic anhydride in pyridine at a temperature below about −20° C. in order to obtain a mixture containing a major proportion of sucrose 6-acetate;
 (b) separating the sucrose 6-acetate by ion-exchange resin chromatography;
 (c) chlorinating the sucrose 6-acetate at the 4,1' and 6' positions with a reagent selected from the group consisting of a Vilsmeier reagent and sulphuryl chloride;
 (c1) peracetylating the chlorinated product with acetic anhydride in pyridine to form TGS penta-acetate; and
 (d) separating and purifying the TGS penta-acetate and subsequently deacetylating the purified material to obtain TGS.

* * * * *